United States Patent
Wimmer et al.

(10) Patent No.: US 6,734,316 B2
(45) Date of Patent: May 11, 2004

(54) ESTERS OF FATTY ACIDS AND JUVENOID ALCOHOLS, AND A METHOD OF THEIR PREPARATION AND USE

(75) Inventors: Zdeněk Wimmer, Prague (CZ); Jelena Kuldová, Prague (CZ); Ivan Hrdý, Prague (CZ); Blanka Bennettová, České Budějovice (CZ)

(73) Assignee: Institute of Organic Chemistry and Biochemistry ASCR, Praha (CZ)

( * ) Notice: Subject to any disclaimer, the term of this patent is extended or adjusted under 35 U.S.C. 154(b) by 81 days.

(21) Appl. No.: 10/182,218

(22) PCT Filed: Jan. 23, 2001

(86) PCT No.: PCT/CZ01/00003
§ 371 (c)(1),
(2), (4) Date: Jul. 25, 2002

(87) PCT Pub. No.: WO01/55081
PCT Pub. Date: Aug. 2, 2001

(65) Prior Publication Data
US 2003/0028047 A1 Feb. 6, 2003

(30) Foreign Application Priority Data
Jan. 27, 2000 (CZ) ........................................ PV2000-317

(51) Int. Cl.[7] .............................................. C07C 57/00

(52) U.S. Cl. ...................... 554/229; 424/405; 424/406

(58) Field of Search .......................... 584/229; 454/405, 454/406

(56) References Cited
PUBLICATIONS

Wimmer et al., Helv. Chim. Acta, vol. 77, No. 5, pp. 1241–1255, 1994.*
Rejzek, Martin et al: "Synthesis and Structure–Activity Relationships of Juvenoids . . ." Helv. Chim. ACTA, (1994) pp. 1243–1246.
Wimmer, Zdenek et al: "Carbamate Series of Juvenoids: Variation of the O–alkyl Substituent" Helv. Chim. ACTA, (1994), pp. 562–563.
Rejzek, Martin et al: "Carbamate and Urea Derivatives with Insect Juvenile Hormone . . ." Chemical Abstracts, vol. 124, No. 8, Feb. 19, 1996, Abstract No. 88603.

* cited by examiner

Primary Examiner—Deborah D. Carr
(74) Attorney, Agent, or Firm—Notaro & Michalos P.C.

(57) ABSTRACT

Esters derived from fatty acids and juvenoid alcohols of the general formula (I), in which X means the oxygen atom or the NH group, Y means the NH group or the oxygen atom, R means methyl, ethyl, 1-propyl, 2-methylethyl or propargyl and R' means saturated or unsaturated alkyl with 4 to 22 carbon atoms. Esters derived from fatty acids and juvenoid alcohols are produced by a reaction of a juvenoid alcohol of the general formula (II), in which X means the oxygen atom or the NH group, Y means the NH group or the oxygen atom and R means methyl, ethyl, 1-propyl, 2-methylethyl or propargy] with a fatty acid chloride of the general formula (III): R'COC1 in which R' means saturated or unsaturated alkyl with 4 to 22 carbon atoms, under the continuous stirring, at 0 to 70° C., using a convenient solvent, as toluene, xylene or benzene and under the presence of a base catalyst, as triethylamine, pyridine or quinoline. The compounds claimed in the claim 1 of the general formula (I) are applied for the insect population density control.

3 Claims, No Drawings

ESTERS OF FATTY ACIDS AND JUVENOID ALCOHOLS, AND A METHOD OF THEIR PREPARATION AND USE

TECHNICAL FIELD

The invention relates to esters derived from fatty acids and juvenoid alcohols, a method of their preparation and use for reduction of insect population density.

BACKGROUND ART

The studies of juvenoids, compounds imitating the effect of natural insect juvenile hormone on insect development and reproduction, have represented an intensively studied field since mid-sixties of this century. A number of monographies and reviews (e.g. Sláma K., Romaňuk M, Šorm F.: Insect Hormones and Bioanalogues, Springer, 1974; Henrick C. A.: Juvenoids; in the book Agrochemicals from Natural Products (C. R. A. Godfrey, ed.), pp. 147–213 (1995); Wimmer Z., Rejzek M., Zarevúcka M., Kuldová J., Hrdý I., Němec V., Romaňuk M.: J. Chem. Ecol. 23, 605–628 (1997)) support this statement. Recently, the attention has also been focused on a modified type of the compounds, which display the effect on insect development and reproduction, on juvenogens (Sláma K., Romaňuk M.: Insect Biochem. 6, 579–586 (1976); Wimmer Z., Rejzek M., Zarevúcka M., Kuldová J., Hrdý I., Němec V., Romaňuk M.: J. Chem. Ecol. 23, 605–628 (1997)). During designing and developing of these new compounds, selected ways of transformation of certain functionalities in the juvenoid molecules have been applied, resulting in a formation of a new functionality, e.g. ester functionality, replacing of the original functionality, e.g. alcoholic functionality, through which transformation physico-chemical properties of the new compound are different from the physico-chemical properties of the original compound. Changes in the physico-chemical properties of the compounds are connected with possible changes of practical application of the new compound as well.

DISCLOSURE OF INVENTION

1. The subjects of this invention are esters derived from fatty acids and juvenoid alcohols of the general formula I,

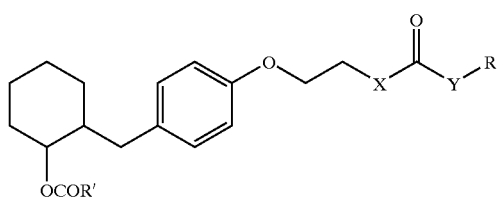

(I)

in which X is oxygen or the NH group,

Y is the NH group or oxygen,

R is methyl, ethyl, 1-propyl, 2-methylethyl or propargyl and

R' is a saturated or an unsaturated alkyl with 4 to 22 carbon atoms.

2. The esters derived from fatty acids and juvenoid alcohols claimed in the claim 1 are prepared using a method that the juvenoid alcohol of the general formula II,

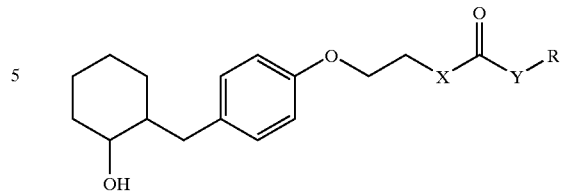

(II)

in which X is the oxygen atom or the NH group,

Y is the NH group or the oxygen atom,

R is methyl, ethyl, 1-propyl, 2-methylethyl or propargyl is allowed to react with the chloride of a fatty acid of the general formula III, $$R'COCl \quad \text{(III)}$$

in which R' is a saturated or an unsaturated allyl with 4 to 22 carbon atoms, under the continuous stirring, at 0 to 70° C., using a convenient solvent, as toluene, xylene or benzene and under the presence of a base catalyst, as triethylamine, pyridine or quinoline.

3. The esters derived from fatty acids and juvenoid alcohols claimed in claim 1 are used for the insect population density control, with special focus on the control of insects of the orders Isoptera, Blattodea, Diptera, Hymenoptera, Orthoptera, Coleoptera, and Lepidoptera. The esters derived from fatty acids and juvenoid alcohols claimed in the claim 1 display different chemical structure compared with the chemical structure of the original juvenoids and display also different physico-chemical properties compared with the properties of the original juvenoids, especially their melting points, through which they display different volatility and polarity, and these differences enable different way of practical application of the compounds claimed in the claim 1 against target insect species, and the esters derived from fatty acids and juvenoid alcohols claimed in claim 1 display higher stability in comparison with the stability of the original juvenoids and are responsible for improved dosage of the compounds claimed in the claim 1 during the screening against insect species. The compounds claimed in the claim 1 also enable a more effective way of practical application and due to their improved physico-chemical properties they also display a longer effect under the field conditions. The compounds claimed in the claim 1 are environmentally safe compounds, which are metabolized in a way through which no toxic residues, persistent in the nature, are left, which display no toxicity towards warm-blooded animals, fish or microorganisms living in water.

Examples are given in the following paragraphs, which make clear the way of preparation of the compounds claimed in the claim 1 of the general formula I.

EXAMPLES

Example 1

Ethyl N-{2-{4-[(cis-2-octadecanoyloxycyclohexyl)methyl]phenoxy}ethyl} carbamate (I)

Octadecanoyl chloride (1.06 mmol) was added to a solution of ethyl N-{2-{4-[(cis-2-hydroxycyclohexyl)methyl]phenoxy}ethyl} carbamate (II; 0.884 mmol) in benzene (10 ml) and in pyridine (0.4 ml), at 0° C. and under stirring during 5 min. Then the cooling bath is removed and the reaction mixture is allowed to stir at 35° C. for 4 h. Then the reaction mixture is worked up by pouring onto a mixture of ice and hydrochloric acid (5:1, 30 ml), and organic layer is extracted with ether (3×30 ml). After drying over sodium sulfate and after removal of the solvent under reduced pressure, the residue is purified by column chromatography on silica gel, affording 500 mg (96%) of the required product claimed in the claim 1 of the general formula I. $^1$H NMR (CDCl$_3$): 0.88 (t, J=6.8 Hz, 3H), 1.23–1.93 (m, 39H), 1.25 (t, J=7.2 Hz, 3H), 2.35 (t, J=7.2 Hz, 2H), 2.39 (dd, J=8.0 a 13.7 Hz, 1H), 2.55 (dd, J=6.8 a 13.7 Hz, 1H), 3.57 (bq, J=5.4 Hz, 2H), 4.00 (t, J=5.1 Hz, 2H), 4.12 (q, J=7.2 Hz, 2H), 4.90 (dt, J=2.6, 2.6 a 4.4 Hz, 1H), 5.11 (bt, J=5.4 Hz, 1H), 6.79 (m, 2H), 7.00 (m, 2H). $^{13}$C NMR (CDCl$_3$): 14.11 (q), 14.60 (q), 20.85 (t), 25.27 (t), 26.97 (t), 29.61 (t, 2C), 29.63 (t, 3C), 29.65 (t, 2C), 29.67 (t, 2C), 29.69 (t, 6C), 31.92 (t), 34.86 (t), 37.76 (t), 40.50 (t), 42.56 (d), 60.92 (t), 66.96 (t), 71.76 (d), 114.26 (d), 129.97 (d), 133.05 (s), 156.66 (s), 156.73 (s), 173.36 (s). IR (CCl$_4$): 3464 (w), 3032 (w), 1729 (s), 1612 (w), 1585 (w), 1510 (s), 1450 (m), 1243 (s), 1219 (s), 1176 (s) cm$^{-1}$. FAB-MS (m/z) 588 (M$^+$+1, 10), 560 (8), 520 (5), 483 (9), 429 (10), 401 (11), 384 (13), 327 (15), 313 (98), 304 (35), 285 (30), 267 (37), 215 (100), 214 (87), 187 (79). M.p.=78–80° C.

Example 2

Ethyl N-{2-{4-[(trans-2-octadecanoyloxycyclohexyl)methyl]phenoxy}ethyl} carbamate (I)

As described in the example 1, 485 mg (95%) of the compound claimed in the claim 1 of the general formula I yielded starting from ethyl N-{2-{4-[(trans-2-hydroxycyclohexyl)-methyl]phenoxy}ethyl} carbamate (II; 0.868 mmol) and octadecanoyl chloride (1.06 mmol) at 35° C., using pyridine as base catalyst. $^1$H NMR (CDCl$_3$): 0.88 (t, J=7.6 Hz, 3H), 1.23–2.01 (m, 39H), 1.25 (t, J=7.1 Hz, 3H), 2.19 (dd, J=9.3 a 13.6 Hz, 1H), 2.29 (t, J=7.6 Hz, 2H), 2.84 (dd, J=3.8 a 13.6 Hz, 1H), 3.57 (bq, J=5.2 Hz, 3H), 4.00 (t, J=5.1 Hz, 2H), 4.12 (q, J=7.1 Hz, 2H), 4.56 (dt, J=4.3, 10.1 a 10.1 Hz, 1H), 5.11 (bt, J=5.2 Hz, 1H), 6.80 (m, 2H), 7.02 (m, 2H). $^{13}$C NMR (CDCl$_3$): 14.10 (q), 14.61 (q), 24.52 (t), 25.08 (t), 29.60 (t, 2C), 29.63 (t, 2C), 29.65 (t, 2C), 29.66 (t, 3C), 29.69 (t, 6C), 29.87 (t), 31.86 (t), 34.75 (t), 37.79 (t), 40.53 (t), 43.89 (d), 60.93 (t), 67.00 (t), 76.47 (d), 114.19 (d), 130.17 (d), 132.86 (s), 156.63 (s), 156.71 (s), 173.59 (s). IR (CCl$_4$): 3464 (w), 3033 (w), 1729 (s), 1612 (w), 1585 (w), 1509 (s), 1451 (m), 1243 (s), 1219 (s), 1176 (s) cm$^{-1}$. FAB-MS (m/z) 588 (M$^+$+1, 5), 503 (7), 459 (10), 429 (14), 415 (10), 401 (6), 371 (11), 327 (10), 313 (23), 307 (21), 304 (25), 285 (10), 257 (18), 232 (19), 215 (100), 214 (63), 187 (62). M.p.=64–65° C.

Example 3

Ethyl N-{2-{4-[(cis-2-(cis-9-octadecenoyl)oxycyclohexyl)methyl]phenoxy}ethyl} carbamate (I)

As described in the example 1, 207 mg (91%) of the compound claimed in the claim 1 of the general formula I yielded starting from ethyl N-{2-{4-[(cis-2-hydroxycyclohexyl)-methyl]phenoxy}ethyl} carbamate (II; 0.389 mmol) and 9-cis-hexadecenoyl chloride (0.5 mmol) at 20° C., using triethylamine as base catalyst. $^1$H NMR (CDCl$_3$): 0.88 (t, J=7.1 Hz, 3H), 1.25–1.74 (mn, 19H), 1.85–1.95 (m, 1H), 1.98–2.05 (m, 2H), 2.36 (t, J=7.7 Hz, 2H), 2.39 (dd, J=7.9 a 13.6 Hz, 1H), 2.55 (dd, J=6.8 a 13.7 Hz, 1H), 3.57 (bq, J=5.3 Hz, 2H), 4.00 (t, J=5.1Hz, 2H), 4.12 (q, J=7.1 Hz, 2H), 4.91 (dt, J=2.7, 2.7 a 4.2 Hz, 1H), 5.12 (bt, J=5.4 Hz, 1H), 5.31–5.38 (m, 2H), 6.79 (m, 2H), 7.00 (m, 2H). $^{13}$C NMR (CDCl$_3$): 14.08 (q), 14.60 (q), 20.87 (t), 22.66 (t), 25.05 (t), 25.25 (t), 27.00 (t), 27.17 (t), 27.22 (t), 29.14 (t), 29.21 (t), 29.23 (t), 29.31 (t), 29.51 (t), 29.64 (t), 29.70 (t), 29.76 (t), 29.99 (t), 31.89 (t), 34.85 (t), 37.75 (t), 40.53 (t), 42.56 (d), 60.92 (t), 66.99 (t), 71.80 (d), 114.30 (d), 129.72 (d), 129.97 (d), 130.00 (d), 133.07 (s), 156.75 (s, 2C), 173.31 (s). IR (CCl$_4$): 3464 (w), 3030 (w), 1729 (s), 1653 (w), 1612 (w), 1585 (w), 1510 (s), 1449 (m), 1243 (s), 1220 (s), 1176 (s), 703 (w) cm$^{-1}$. FAB-MS (m/z) 586 (M$^+$+1, 5), 391 (5), 304 (19), 176 (8), 149 (10), 116 (100), 107 (44), 88 (70). Mp.=39–40° C.

Example 4

Ethyl N-{2-{4-[(trans-2-(cis-9-octadecenoyl)oxycyclohexyl)methyl]phenoxy}ethyl} carbamate (I)

As described in the example 1, 209.5 mg (92%) of the compound claimed in the claim 1 of the general formula I yielded starting from ethyl N-{2-{4-[(cis-2-hydroxycyclohexyl)-methyl]phenoxy}ethyl} carbamate (II; 0.389 mmol) and 9-cis-hexadecenoyl chloride (0.5 mmol) at 20° C., using triethylamine as base catalyst. $^1$H NMR (CDCl$_3$): 0.90 (t, J=7.1 Hz, 3H), 1.20–1.78 (m, 31H), 1.25 (t, J=7.1 Hz, 3H), 1.91–2.06 (m, 2H), 2.19 (dd, J=9.4 a 13.7 Hz, 1H), 2.35 (t, J=7.6 Hz, 2H), 2.84 (dd, J=3.6 a 13.7 Hz, 1H), 3.57 (bq, J=5.4 Hz, 2H), 4.00 (t, J=5.1 Hz, 2H), 4.12 (q, J=7.1 Hz, 2H), 4.57 (dt, J=4.3, 10.1 a 10.1 Hz, 1H), 5.10 (bt, J=5.3 Hz, 1H), 5.30–5.41 (m, 2H), 6.80 (m, 2H), 7.02 (m, 2H). $^{13}$C NMR (CDCl$_3$): 14.09 (q), 14.62 (q), 22.67 (t), 24.53 (t), 25.08 (t), 25.14 (t), 27.17 (t), 27.22 (t), 29.18 (t), 29.31 (t), 29.32 (t), 29.52 (t), 29.60 (t), 29.70 (t), 29.77 (t), 29.89 (t), 31.86 (t), 31.90 (t), 34.75 (t), 37.81 (t), 40.56 (t), 43.90 (d), 60.94 (t), 67.04 (t), 76.48 (d), 114.23 (d), 129.75 (d), 129.99 (d), 130.17 (d), 132.87 (s), 156.50 (s), 156.74 (s), 173.53 (s). IR (CCl$_4$): 3464 (w), 3032 (w), 1728 (s), 1654 (w), 1612 (w), 1585 (w), 1510 (s), 1451 (m), 1243 (s), 1221 (s), 1176 (s), 705 (w) cm$^{-1}$. FAB-MS (m/z) 586 (M$^+$+1, 2), 558 (1), 514 (1), 391 (1), 304 (10), 222 (3), 188 (2), 176 (4), 149 (9), 116 (100), 107 (15), 88 (39). M.p.=36–37° C.

Example 5

Ethyl N-{2-{4-[(cis-2-hexadecanoyloxycyclohexyl)methyl]phenoxy}ethyl} carbamate (I)

As described in the example 1, 225 mg (95%) of the compound claimed in the claim 1 of the general formula I yielded starting from ethyl N-{2-{4-[(cis-2-hydroxycyclohexyl)-methyl]phenoxy}ethyl} carbamate (II; 0.424 mmol) and hexadecanoylchloride (0.509 mmol) at 70° C., using quinoline as base catalyst. $^1$H NMR (CDCl$_3$): 0.88 (t, J=7.1 Hz, 3H), 1.25 (t, J=7.1 Hz, 3H), 1.25–1.74 (m, 34H), 1.90 (m, 1H), 2.36 (t, J=7.7 Hz, 2H), 2.39 (dd, J=7.9 a 13.6 Hz, 1H), 2.55 (dd, J=6.8 a 13.6 Hz, 1H), 3.57 (bq, J=5.3 Hz, 2H), 4.00 (t, J=5.0 Hz, 2H), 4.12 (q, J=7.1 Hz, 2H), 4.90 (dt, J=2.6, 2.6 and 4.3 Hz, 1H), 5.10 (bt, J=5.4 Hz, 1H), 6.79 (m, 2H), 7.00 (m, 2H). $^{13}$C NMR (CDCl$_3$): 14.10 (q), 14.62 (q), 22.68 (t), 25.29 (t), 27.01 (t), 29.27 (t), 29.33 (t), 29.35 (t), 29.52 (t), 29.62 (t, 2C), 29.65 (t, 2C), 29.68 (t, 2C), 29.69 (t, 2C), 30.00 (t), 31.92 (t), 34.88 (t), 37.76 (t), 40.54 (t), 42.58 (d), 60.93 (t), 67.00 (t), 71.79 (d), 114.32 (d), 129.98 (d), 133.10 (s), 156.76 (s, 2C), 173.33 (s). IR (CCl$_4$): 3464 (w), 3032 (w), 1729 (s), 1612 (w), 1585 (w), 1510 (s), 1449 (m), 1272 (m) cm$^{-1}$. FAB-MS (m/z) 560 (M$^+$+1, 3), 476 (2), 415 (1), 405 (2), 391 (3), 279 (19), 257 (5), 215 (9), 201 (30), 181 (16), 165 (17), 149 (100), 110 (60). Mp.= 78–80° C.

Example 6

Ethyl N-{2-{4-[(trans-2-hexadecanoyloxycyclohexyl)methyl]phenoxy}ethyl} carbamate (I)

As described in the example 1, 236 mg (99%) of the compound claimed in the claim 1 of the general formula I yielded starting from ethyl N-{2-{4-[(cis-2-hydroxycyclohexyl)-methyl]phenoxy}ethyl} carbamate (II; 0.424 mmol) and hexadecanoylchloride (0.509 mmol) at 70° C., using quinoline as base catalyst. $^1$H NMR (CDCl$_3$): 0.88 (t, J=7.1H, 3H), 0.89–1.74 (m, 35H), 1.25 (t, J=7.1 Hz, 3H), 2.19 (dd, J=9.3 a 13.6 Hz, 1H), 2.29 (t, J=7.5 Hz, 2H), 2.84 (dd, J=3.7 a 13.6 Hz, 1H), 3.57 (bq, J=5.2 Hz, 2H), 4.00 (t, J=5.1 Hz, 2H), 4.12 (q, J=7.1 Hz, 2H), 4.56 (dt, 3=4.4, 10.1 a 10.1 Hz, 1H), 5.10 (bt, 3=5.3 Hz, 1H), 6.80 (m, 2H), 7.03 (m, 2H). $^{13}$C NMR (CDCl$_3$): 14.10 (q), 14.62 (q), 24.53 (t), 25.15 (t), 29.20 (t), 29.28 (t), 29.35 (t, 2C), 29.48 (t, 2C), 29.65 (t, 2C), 29.68 (t, 4C), 29.89 (t), 29.90 (t), 31.93 (t), 34.76 (t), 37.81 (t), 40.54 (t), 43.90 (d), 60.92 (t), 67.03 (t), 76.47 (d), 114.22 (d), 130.18 (d), 132.89 (s), 156.74 (s, 2C), 173.56 (s). IR (CCl$_4$): 3464 (w), 3033 (w), 1728 (s), 1612 (w), 1585 (w), 1509 (s), 1451 (m), 1243 (s), 1219 (s), 1176 (s) cm$^{-1}$. FAB-MS (m/z) 560 (M$^+$+1, 8), 488 (3), 396 (1), 368 (1), 340 (1), 303 (12), 262 (3), 115 (100), 88 (40), M.p.=67–68° C.

Example 7

Ethyl N-{2-{4-[(cis-2-butanoyloxycyclohexyl) methyl]phenoxy}ethyl} carbamate (I)

As described in the example 1, 142 mg (94%) of the compound claimed in the claim 1 of the general formula I yielded starting from ethyl N-{2-{4-[(cis-2-hydroxycyclohexyl)-methyl]phenoxy}ethyl} carbamate (II; 0.384 mmol) and butanoyl chloride (0.418 mmol) at 20° C., using pyridine as base catalyst. $^1$H NMR (CDCl$_3$): 1.00 (t, J=7.4 Hz, 3H), 1.20–1.51 (m, 8H), 1.24 (t, J=7.2 Hz, 3H), 1.72 (m, 2H), 1.91 (m, 1H), 2.35 (t, J=7.5 Hz, 2H), 2.39 (dd, J=8.2 a 13.6 Hz, 1H), 2.55 (dd, J=6.9 a 13.6 Hz, 1H), 3.57 (bq, J=5.3 Hz, 2H), 4.00 (t, J=5.1 Hz, 2H), 4.12 (q, J=7.2 Hz, 2H), 4.91 (dt, J=2.6, 2.6 a 4.4 Hz, 1H), 5.11 (bt, J=5.3 Hz, 1H), 6.79 (m, 2H), 7.00 (m, 2H). $^{13}$C NMR (CDCl$_3$): 13.78 (q), 14.61 (q), 18.72 (t), 20.86 (t), 25.05 (t), 26.99 (t), 29.99 (t), 36.78 (t), 37.74 (t), 40.52 (t), 42.55 (d), 60.91 (t), 66.99 (t), 71.77 (d), 114.30 (d), 129.97 (d), 133.06 (s), 156.64 (s), 156.74 (s), 173.13 (s). IR (CCl$_4$): 3464 (w), 3033 (w), 1729 (s), 1612 (w), 1585 (w), 1510 (s), 1243 (s), 1176 (s), 1095 (m) cm$^{-1}$. FAB-MS (m/z) 392 (M$^+$+1, 35), 304 (21), 231 (8), 154 (9), 137 (9), 116 (100), 107 (21), 88 (42), 71 (13). M.p.=82–84° C.

Example 8

Ethyl N-{2-{4-[(trans-2-butanoyloxycyclohexyl) methyl]phenoxy}ethyl} carbamate (I)

As described in the example 1, 113 mg (93%) of the compound claimed in the claim 1 of the general formula I yielded starting from ethyl N-{2-{4-[(cis-2-hydroxycyclohexyl)-methyl]phenoxy}ethyl} carbamate (II; 0.384 mmol) and butanoyl chloride (0.418 mmol) at 20° C., using pyridine as base catalyst. $^1$H NMR (CDCl$_3$): 0.96 (t, J=7.4 Hz, 3H), 1.24 (t, J=7.2 Hz, 3H), 1.26–1.78 (m, 10H), 2.00 (m, 1H), 2.19 (dd, J=9.3 a 13.6 Hz, 1H), 2.27 (t, J=7.5 Hz, 2H), 2.84 (dd, J=3.8 a 13.6 Hz, 1H), 3.57 (bq, J=5.3 Hz, 2H), 4.00 (t, J=5.1 Hz, 2H), 4.12 (q, J=7.2 Hz, 2H), 4.56 (dt, J=4.4, 10.1 a 10.1 Hz, 1H), 5.12 (bt, J=5.3 Hz, 1H), 6.80 (m, 2H), 7.03 (m, 2H). $^{13}$C NMR (CDCl$_3$): 13.70 (q), 14.61 (q), 18.60 (t), 24.52 (t), 25.09 (t), 29.91 (t), 31.87 (t), 36.64 (t), 37.84 (t), 40.56 (t), 43.89 (d), 60.92 (t), 67.05 (t), 76.48 (d), 114.25 (d), 130.16 (d), 132.90 (s), 156.66 (s), 156.75 (s), 173.35 (s). IR (CCl$_4$): 3464 (w), 3034 (w), 1728 (s), 1612 (w), 1585 (w), 1509 (s), 1243 (s), 1177 (s), 1101 (m), 1089 (m) cm$^{-1}$. FAB-MS (m/z) 392 (M$^+$+1, 17), 320 (6), 304 (11), 222 (6), 133 (6), 116 (100), 107 (37), 88 (45), 71 (13). M.p.=60–62° C.

Example 9

A Way of Screening of the Biological Activity of the Compound Claimed in the claim 1 of the General Formula I Against Blowfly Neobellieria (Sarcophaga) bullata A solution of the compound claimed in the claim 1 of the general formula I in acetone (0.1%) was applied in a quantity of 5 microliters (5 micrograms per female) to the upper part of thorax. Treated blowfly females were caged up together with intact (non-treated) males for mating. The females were dissected in periodic intervals, and the morphological state of ovaries was checked—the egg shape, the degree of yolk deposition in the first and in the second egg chamber, a level of resorption of ovarioles and egg hatchability. The transformed (affected) ovaries were examined histologically.

Example 10

A Way of Screening of the Biological Activity of the Compound Claimed in the claim 1 of the General Formula I Against Termite Prorhinotermes Simplex Termites have only a sample of food treated with the compound claimed in the claim 1 of the general formula I in the force feeding test (FF), but a choice between a sample of food treated with the compound claimed in the claim 1 of the general formula I and a reference sample of food treated with acetone only. A treatment of the food samples with the compound I claimed in the claim 1 has been made in at least two concentrations, 500 ppm and 5 ppm. A number of 60 pseudergates was exposed to a treatment in each test, and each test is twice repeated. Each test has 16 days duration. The induction of the soldier caste differentiation has been evaluated as the juvenilizing effect. The result is given in percents of the number of surviving individuals. The juvenoid methoprene has been used as the reference compound for testing of the biological activity of the compound I claimed in the claim 1. The results of screening of several structures corresponding the general formula I claimed in the claim 1 in a concentration of 500 ppm are given in Table 1.

TABLE 1

Juvenilizing effect of the tested structures of the general formula I and that of methoprene in the concentrations of 500 ppm on termite *Prorrhinotermes simplex*

| Compound (the reference compound or the compound of the general formula I) | Method | Juvenilizing effect [%] |
|---|---|---|
| Methoprene | FF | 1.3 |
| Ethyl N-{2-{4-[(cis-2-octadecanoyloxycyclohexyl)-methyl]phenoxy}ethyl} carbamate (I) | FF | 40.0 |
| Ethyl N-{2-{4-[(trans-2-octadecanoyloxycyclohexyl)-methyl]phenoxy}ethyl} carbamate (I) | FF | 70.0 |
| Ethyl N-{2-{4-[(cis-2-(cis-9-octadecenoyl)oxycyclohexyl)-methyl]phenoxy}ethyl} carbamate (I) | FF | 93.7 |
| Ethyl N-{2-{4-[(trans-2-(cis-9-octadecenoyl)oxycyclohexyl)-methyl]phenoxy}ethyl} carbamate (I) | FF | 64.7 |
| Ethyl N-{2-{4-[(cis-2-hexadecanoyloxycyclohexyl)-methyl]phenoxy}ethyl} carbamate (I) | FF | 89.1 |
| Ethyl N-{2-{4-[(trans-2-hexadecanoyloxycyclohexyl)-methyl]phenoxy}ethyl} carbamate (I) | FF | 90.1 |
| Ethyl N-{2-{4-[(cis-2-butanoyloxycyclohexyl)-methyl]phenoxy}ethyl} carbamate (I) | FF | 86.1 |
| Ethyl N-{2-{4-[(trans-2-butanoyloxycyclohexyl)-methyl]phenoxy}ethyl} carbamate (F) | FF | 87.4 |

Industrial Application

The compound I claimed in the claim 1 are applicable in the areas of insect population density control, especially in the area of social hygiene, against cockroaches, termites and ants in the restaurant-type facilities, hospitals, journal depositories, stories, houses etc. or in the agricultural production, against moths, locusts, beetles, flies, mosquitoes etc.

What is claimed is:

1. Esters derived from fatty acids and juvenoid alcohols of the general formula I,

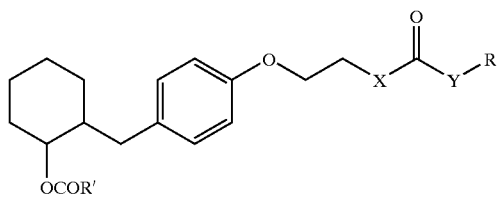

in which X means the oxygen atom or the NH group,
Y means the NH group or the oxygen atom,
R means methyl, ethyl, 1-propyl, 2-methylethyl or propargyl and
R' means saturated or unsaturated alkyl with 4 to 22 carbon atoms.

2. A method of preparation of the compounds claimed in the claim 1 of the general formula I based on a reaction of the juvenoid alcohol of the general formula II,

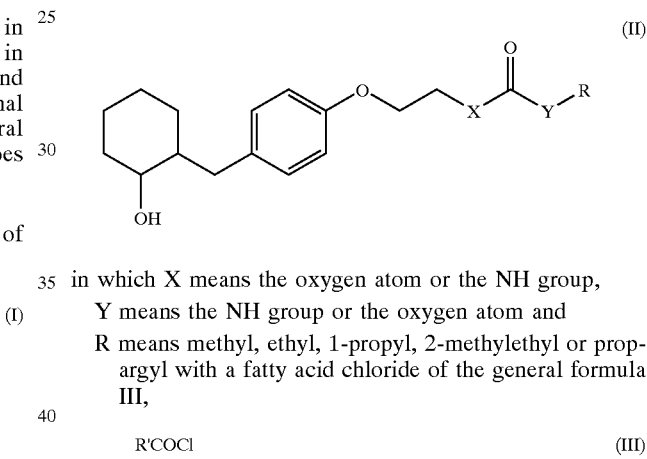

in which X means the oxygen atom or the NH group,
Y means the NH group or the oxygen atom and
R means methyl, ethyl, 1-propyl, 2-methylethyl or propargyl with a fatty acid chloride of the general formula III, R'COCl (III)

in which R' means saturated or unsaturated alkyl with 4 to 22 carbon atoms, under the continuous stirring, at 0 to 70° C., using a convenient solvent, as toluene, xylene or benzene and under the presence of a base catalyst, as triethylamine, pyridine or quinoline.

3. The application of the compounds claimed in the claim 1 of the general formula I for the insect population density control, focused on control of insects of the orders Isoptera, Blattodea, Diptera, Hymenoptera, Orthoptera, Coleoptera, and Lepidoptera.

* * * * *